(12) United States Patent
Borremans

(10) Patent No.: US 8,273,923 B2
(45) Date of Patent: Sep. 25, 2012

(54) PROCESS FOR MANUFACTURING A CHLOROHYDRIN

(75) Inventor: Daniel Borremans, Mont-sur-Marchienne (BE)

(73) Assignee: Solvay (Societe Anonyme), Brussels (BE)

( * ) Notice: Subject to any disclaimer, the term of this patent is extended or adjusted under 35 U.S.C. 154(b) by 481 days.

(21) Appl. No.: 12/600,018

(22) PCT Filed: May 30, 2008

(86) PCT No.: PCT/EP2008/056688
§ 371 (c)(1),
(2), (4) Date: Nov. 13, 2009

(87) PCT Pub. No.: WO2008/145729
PCT Pub. Date: Dec. 4, 2008

(65) Prior Publication Data
US 2010/0305367 A1    Dec. 2, 2010

Related U.S. Application Data

(60) Provisional application No. 61/013,676, filed on Dec. 14, 2007.

(30) Foreign Application Priority Data

Jun. 1, 2007  (EP) .................................. 07109461

(51) Int. Cl.
C07C 29/60 (2006.01)
C07C 29/62 (2006.01)
(52) U.S. Cl. ........................ 568/841; 568/844
(58) Field of Classification Search ................. 568/841, 568/844
See application file for complete search history.

(56) References Cited

U.S. PATENT DOCUMENTS

| | | | |
|---|---|---|---|
| 280,893 | A | 7/1883 | Baujard |
| 2,060,715 | A | 11/1936 | Arvin |
| 2,063,891 | A | 12/1936 | Dreyfus |
| 2,144,612 | A | 1/1939 | Britton et al. |
| 2,198,600 | A | 4/1940 | Britton et al. |
| 2,248,635 | A | 7/1941 | Marple et al. |
| 2,319,876 | A | 5/1943 | Moss |
| 2,444,333 | A | 6/1948 | Castan |
| 2,505,735 | A | 4/1950 | Halbedel |
| 2,726,072 | A | 12/1955 | Herman |
| 2,811,227 | A | 10/1957 | O'Connor |
| 2,829,124 | A | 4/1958 | Napravnik et al. |
| 2,860,146 | A | 11/1958 | Furman et al. |
| 2,876,217 | A | 3/1959 | Paschall |
| 2,945,004 | A | 7/1960 | Greenlee |
| 2,960,447 | A | 11/1960 | Anderson et al. |
| 3,026,270 | A | 3/1962 | Robinson, Jr. |
| 3,061,615 | A | 10/1962 | Viriot et al. |
| 3,121,727 | A | 2/1964 | Baliker et al. |
| 3,135,705 | A | 6/1964 | Vandenberg |
| 3,158,580 | A | 11/1964 | Vandenberg |
| 3,158,581 | A | 11/1964 | Vandenberg |
| 3,247,227 | A | 4/1966 | White |
| 3,260,059 | A | 7/1966 | Rosenberg et al. |
| 3,341,491 | A | 9/1967 | Robinson et al. |
| 3,355,511 | A | 11/1967 | Schwarzer |
| 3,385,908 | A | 5/1968 | Schwarzer |
| 3,445,197 | A | 5/1969 | Resh et al. |
| 3,457,282 | A | 7/1969 | Polak et al. |
| 3,618,295 | A | 11/1971 | Geiger et al. |
| 3,711,388 | A | 1/1973 | Gritzner |
| 3,766,221 | A | 10/1973 | Becker |
| 3,839,169 | A | 10/1974 | Moyer |
| 3,865,886 | A | 2/1975 | Schindler et al. |
| 3,867,166 | A | 2/1975 | Sullivan |
| 3,954,581 | A | 5/1976 | Carlin |
| 3,968,178 | A | 7/1976 | Obrecht et al. |
| 4,003,723 | A | 1/1977 | Schafer et al. |
| 4,011,251 | A | 3/1977 | Tjurin et al. |
| 4,024,301 | A | 5/1977 | Witenhafer et al. |
| 4,127,594 | A | 11/1978 | Anderson et al. |
| 4,173,710 | A | 11/1979 | Boulet et al. |
| 4,197,399 | A | 4/1980 | Noel et al. |
| 4,220,529 | A | 9/1980 | Daude-Lagrave |
| 4,255,470 | A | 3/1981 | Cohen et al. |
| 4,294,776 | A | 10/1981 | Hardy et al. |
| 4,390,680 | A | 6/1983 | Nelson |
| 4,405,465 | A | 9/1983 | Moore et al. |
| 4,415,460 | A | 11/1983 | Suciu et al. |
| 4,464,517 | A | 8/1984 | Makino et al. |
| 4,499,255 | A | 2/1985 | Wang et al. |
| 4,595,469 | A | 6/1986 | Foller |
| 4,609,751 | A | 9/1986 | Hajjar |

(Continued)

FOREIGN PATENT DOCUMENTS

CN    1296003 A    5/2001

(Continued)

OTHER PUBLICATIONS

U.S. Appl. No. 12/745,802, Patrick Gilbeau et al.

(Continued)

*Primary Examiner* — Elvis O Price
(74) *Attorney, Agent, or Firm* — Beatrice C. Ortego

(57) ABSTRACT

A process for manufacturing a chlorohydrin by reacting a polyhydroxylated-aliphatic hydrocarbon, an ester of a polyhydroxylated-aliphatic hydrocarbon, or a mixture thereof with a chlorinating agent in a reactor containing a liquid reaction medium wherein the chlorinating agent is used at least partially in the gaseous form, and wherein said reactor is stirred by means of a stirring system comprising at least one radial-flow impeller and at least one axial-flow impeller.

15 Claims, 3 Drawing Sheets

U.S. PATENT DOCUMENTS

| | | | |
|---|---|---|---|
| 4,634,784 A | 1/1987 | Nagato et al. |
| 4,655,879 A | 4/1987 | Brockmann et al. |
| 4,935,220 A | 6/1990 | Schneider et al. |
| 4,960,953 A | 10/1990 | Jakobson et al. |
| 4,973,763 A | 11/1990 | Jakobson et al. |
| 4,990,695 A | 2/1991 | Buenemann et al. |
| 5,041,688 A | 8/1991 | Jakobson et al. |
| 5,200,163 A | 4/1993 | Henkelmann et al. |
| 5,278,260 A | 1/1994 | Schaffner et al. |
| 5,286,354 A | 2/1994 | Bard et al. |
| 5,344,945 A | 9/1994 | Grunchard |
| 5,359,094 A | 10/1994 | Teles et al. |
| 5,393,428 A | 2/1995 | Dilla et al. |
| 5,445,741 A | 8/1995 | Dilla et al. |
| 5,478,472 A | 12/1995 | Dilla et al. |
| 5,567,359 A | 10/1996 | Cassidy et al. |
| 5,578,740 A | 11/1996 | Au et al. |
| 5,679,839 A | 10/1997 | Armand et al. |
| 5,710,350 A | 1/1998 | Jeromin et al. |
| 5,731,476 A | 3/1998 | Shawl et al. |
| 5,744,655 A | 4/1998 | Thomas et al. |
| 5,779,915 A | 7/1998 | Becker et al. |
| 5,908,946 A | 6/1999 | Stern et al. |
| 5,993,974 A | 11/1999 | Fukushima et al. |
| 6,024,839 A | 2/2000 | Schufeldt |
| 6,142,458 A | 11/2000 | Howk |
| 6,177,599 B1 | 1/2001 | Cowfer et al. |
| 6,270,682 B1 | 8/2001 | Santen et al. |
| 6,288,248 B1 | 9/2001 | Strebelle et al. |
| 6,288,287 B2 | 9/2001 | Ueoka et al. |
| 6,350,888 B1 | 2/2002 | Strebelle et al. |
| 6,350,922 B1 | 2/2002 | Vosejpka et al. |
| 6,521,794 B2 | 2/2003 | Hirota |
| 6,719,957 B2 | 4/2004 | Brady, Jr. et al. |
| 6,740,633 B2 | 5/2004 | Norenberg et al. |
| 6,831,201 B2 | 12/2004 | Katsuura et al. |
| 7,126,032 B1 | 10/2006 | Aiken |
| 7,128,890 B2 | 10/2006 | Ollivier |
| 865,727 A1 | 9/2007 | Queneau |
| 7,557,253 B2 | 7/2009 | Gilbeau |
| 7,584,629 B2 | 9/2009 | Sohn et al. |
| 7,615,670 B2 | 11/2009 | Gilbeau |
| 2001/0014763 A1 | 8/2001 | Ueoka et al. |
| 2003/0209490 A1 | 11/2003 | Camp et al. |
| 2004/0016411 A1 | 1/2004 | Joyce et al. |
| 2004/0024244 A1 | 2/2004 | Walsdorff et al. |
| 2004/0150123 A1 | 8/2004 | Strofer et al. |
| 2004/0179987 A1 | 9/2004 | Oku et al. |
| 2004/0232007 A1 | 11/2004 | Carson et al. |
| 2005/0261509 A1 | 11/2005 | Delfort et al. |
| 2006/0052272 A1 | 3/2006 | Meli et al. |
| 2006/0079433 A1 | 4/2006 | Hecht et al. |
| 2006/0123842 A1 | 6/2006 | Sohn et al. |
| 2007/0112224 A1 | 5/2007 | Krafft et al. |
| 2007/0293707 A1 | 12/2007 | Wolfert et al. |
| 2008/0146753 A1 | 6/2008 | Woike et al. |
| 2008/0154050 A1 | 6/2008 | Gilbeau |
| 2008/0161613 A1 | 7/2008 | Krafft et al. |
| 2008/0194847 A1 | 8/2008 | Krafft et al. |
| 2008/0194849 A1 | 8/2008 | Krafft et al. |
| 2008/0194851 A1 | 8/2008 | Gilbeau |
| 2008/0200642 A1 | 8/2008 | Krafft |
| 2008/0200701 A1 | 8/2008 | Krafft et al. |
| 2008/0207930 A1 | 8/2008 | Gilbeau et al. |
| 2008/0214848 A1 | 9/2008 | Krafft et al. |
| 2008/0281132 A1 | 11/2008 | Krafft et al. |
| 2009/0022653 A1 | 1/2009 | Strebelle et al. |
| 2009/0131631 A1 | 5/2009 | Krafft et al. |
| 2009/0198041 A1 | 8/2009 | Krafft et al. |
| 2009/0270588 A1 | 10/2009 | Krafft et al. |
| 2009/0275726 A1 | 11/2009 | Krafft et al. |
| 2010/0029959 A1 | 2/2010 | Fan et al. |
| 2011/0028683 A1 | 2/2011 | Gilbeau et al. |

FOREIGN PATENT DOCUMENTS

| | | |
|---|---|---|
| CN | 101041421 | 9/2007 |
| DE | 58396 C | 8/1891 |
| DE | 180668 C | 1/1906 |
| DE | 197308 C | 11/1906 |
| DE | 238341 C | 3/1908 |
| DE | 197309 C | 4/1908 |
| DE | 869 193 | 3/1953 |
| DE | 1041488 B | 10/1958 |
| DE | 1075103 B | 2/1960 |
| DE | 1226554 B | 10/1966 |
| DE | 2 241 393 | 2/1974 |
| DE | 25 21 813 | 12/1975 |
| DE | 3003819 A1 | 8/1981 |
| DE | 3243617 | 5/1984 |
| DE | 216471 A1 | 12/1984 |
| DE | 3721003 C1 | 12/1988 |
| DE | 43 02 306 | 8/1994 |
| DE | 10203914 C1 | 10/2003 |
| DE | 10254709 A1 | 6/2004 |
| EP | 0 296 341 | 12/1988 |
| EP | 0347618 A2 | 12/1989 |
| EP | 0358255 A1 | 3/1990 |
| EP | 0421379 A1 | 4/1991 |
| EP | 0 452 265 | 10/1991 |
| EP | 0518765 A1 | 12/1992 |
| EP | 0522382 A1 | 1/1993 |
| EP | 0535949 B1 | 4/1993 |
| EP | 0561441 A1 | 9/1993 |
| EP | 0563720 A1 | 10/1993 |
| EP | 0568389 A1 | 11/1993 |
| EP | 0582201 A2 | 2/1994 |
| EP | 0 618 170 | 10/1994 |
| EP | 0 916 624 | 5/1999 |
| EP | 0919551 A1 | 6/1999 |
| EP | 0 774 450 | 2/2000 |
| EP | 1059278 A2 | 12/2000 |
| EP | 1106237 A1 | 6/2001 |
| EP | 1153887 A2 | 11/2001 |
| EP | 1163946 A1 | 12/2001 |
| EP | 1298154 A1 | 4/2003 |
| EP | 1411027 A1 | 4/2004 |
| EP | 1752435 A1 | 2/2007 |
| EP | 1752436 A1 | 2/2007 |
| EP | 1760060 A1 | 3/2007 |
| EP | 1762556 A1 | 3/2007 |
| EP | 1770081 A1 | 4/2007 |
| EP | 1772446 A1 | 4/2007 |
| EP | 1775278 A1 | 4/2007 |
| EP | 2 085 364 | 8/2009 |
| FR | 1 306 231 | 10/1961 |
| FR | 1 417 388 | 10/1964 |
| FR | 1476073 A | 4/1967 |
| FR | 1 577 792 | 8/1968 |
| FR | 2151107 | 4/1973 |
| FR | 2180138 | 5/1973 |
| FR | 2 217 372 | 2/1974 |
| FR | 2565229 A1 | 12/1985 |
| FR | 2752242 A1 | 2/1998 |
| FR | 2862644 A1 | 5/2005 |
| FR | 2868419 A1 | 10/2005 |
| FR | 2869612 A1 | 11/2005 |
| FR | 2869613 A1 | 11/2005 |
| FR | 2872504 A1 | 1/2006 |
| FR | 2881732 A1 | 8/2006 |
| FR | 2885903 A1 | 11/2006 |
| FR | 2 912 743 | 8/2008 |
| FR | 2 913 683 | 9/2008 |
| FR | 2913683 A1 | 9/2008 |
| FR | 2 917 411 | 12/2008 |
| FR | 2918058 A1 | 1/2009 |
| FR | 2925045 A1 | 6/2009 |
| FR | 2929611 A1 | 10/2009 |
| FR | 2935699 A1 | 3/2010 |
| FR | 2935968 A1 | 3/2010 |
| GB | 14767 A | 0/1914 |
| GB | 406345 | 8/1932 |
| GB | 404938 A | 1/1934 |
| GB | 467481 A | 6/1937 |
| GB | 541357 A | 11/1941 |
| GB | 679536 A | 9/1952 |
| GB | 702143 A | 1/1954 |

| | | | |
|---|---|---|---|
| GB | 736641 A | 9/1955 |
| GB | 799567 A | 8/1958 |
| GB | 984446 A | 2/1965 |
| GB | 984633 A | 3/1965 |
| GB | 1083594 A | 9/1967 |
| GB | 1286893 A | 8/1972 |
| GB | 1387668 A | 3/1975 |
| GB | 1 493 538 | 4/1975 |
| GB | 1414976 A | 11/1975 |
| GB | 2173496 A | 10/1986 |
| GB | 2336584 A | 10/1999 |
| HU | 2002-003023 | 3/2004 |
| JP | 3927230 B2 | 11/1939 |
| JP | 50-062909 | 5/1975 |
| JP | 51021635 B | 7/1976 |
| JP | 55041858 A | 3/1980 |
| JP | 5629572 | 3/1981 |
| JP | 5699432 | 8/1981 |
| JP | 61 112066 A | 5/1986 |
| JP | 62242638 A | 10/1987 |
| JP | 63195288 A | 8/1988 |
| JP | 2-137704 | 5/1990 |
| JP | 03014527 A | 1/1991 |
| JP | 3223267 A | 10/1991 |
| JP | 03223267 A | 10/1991 |
| JP | 04089440 A | 3/1992 |
| JP | 04-217637 | 8/1992 |
| JP | 625196 B2 | 4/1994 |
| JP | 06184024 A | 7/1994 |
| JP | 6321852 A | 11/1994 |
| JP | 859593 | 3/1996 |
| JP | 09-299953 | 11/1997 |
| JP | 10139700 A | 5/1998 |
| JP | 1998218810 A | 8/1998 |
| JP | 2001-037469 | 2/2001 |
| JP | 2001-213827 A | 8/2001 |
| JP | 2001-261308 | 9/2001 |
| JP | 2001-1261581 A | 9/2001 |
| JP | 2002-02033 A2 | 1/2002 |
| JP | 20020038195 A | 2/2002 |
| JP | 2002-363153 A | 12/2002 |
| JP | 2003-89680 A | 3/2003 |
| JP | 2003081891 A | 3/2003 |
| JP | 2005007841 A2 | 1/2005 |
| JP | 2005097177 A2 | 4/2005 |
| JP | 2007-006898 | 1/2007 |
| JP | 2009-263338 | 11/2009 |
| KR | 900004513 | 11/1987 |
| KR | 1019920003099 B1 | 4/1992 |
| KR | 10-514819 B1 | 9/2005 |
| PL | 136598 | 3/1986 |
| PL | 162910 | 1/1994 |
| SU | 123153 | 1/1959 |
| SU | 1125226 | 11/1984 |
| SU | 1159716 | 6/1985 |
| SU | 1685969 | 10/1991 |
| WO | WO 95/14639 | 6/1995 |
| WO | WO 96/07617 | 3/1996 |
| WO | WO 96/15980 | 5/1996 |
| WO | WO 97/48687 | 12/1997 |
| WO | WO 98/37024 | 8/1998 |
| WO | WO 99/14208 | 3/1999 |
| WO | WO 9932397 A1 | 7/1999 |
| WO | WO 0186220 A2 | 11/2001 |
| WO | WO 02/26672 A2 | 4/2002 |
| WO | WO 03/064357 | 8/2003 |
| WO | WO 2004/056758 | 7/2004 |
| WO | WO 2005021476 A1 | 3/2005 |
| WO | WO 2005054167 A1 | 6/2005 |
| WO | WO 2005/097722 | 10/2005 |
| WO | WO 2005/115954 | 12/2005 |
| WO | WO 2005/116004 | 12/2005 |
| WO | WO 2006020234 A1 | 2/2006 |
| WO | WO 200/1100319 A1 | 9/2006 |
| WO | WO 2006/100311 | 9/2006 |
| WO | WO 2006/100312 | 9/2006 |
| WO | WO 2006/100313 | 9/2006 |
| WO | WO 2006/100314 A1 | 9/2006 |
| WO | WO 2006/100315 A2 | 9/2006 |
| WO | WO 2006/100316 A1 | 9/2006 |
| WO | WO 2006/100317 A1 | 9/2006 |
| WO | WO 2006/100318 A2 | 9/2006 |
| WO | WO 2006/100320 A2 | 9/2006 |
| WO | WO 2006/106153 A2 | 10/2006 |
| WO | WO 2006/106154 A1 | 10/2006 |
| WO | WO 2006/106155 A2 | 10/2006 |
| WO | WO 2007/054505 A2 | 5/2007 |
| WO | WO 2007/144335 | 12/2007 |
| WO | WO 2008/101866 | 8/2008 |
| WO | WO 2008/107468 | 9/2008 |
| WO | WO 2008/110588 | 9/2008 |
| WO | WO 2008/147473 | 12/2008 |
| WO | WO 2008/152043 | 12/2008 |
| WO | WO 2008/152044 | 12/2008 |
| WO | WO 2008/152045 | 12/2008 |
| WO | WO 2009/000773 | 12/2008 |
| WO | WO 2009/016149 A2 | 2/2009 |
| WO | WO2009/043796 A1 | 4/2009 |
| WO | WO 2009/077528 | 6/2009 |
| WO | WO 2009/077528 A1 | 6/2009 |
| WO | WO 2009/095429 A1 | 8/2009 |
| WO | WO 2009/121853 | 10/2009 |
| WO | WO2009/121853 A1 | 10/2009 |
| WO | WO 2010/029039 | 3/2010 |
| WO | WO 2010/029039 A1 | 3/2010 |
| WO | WO 2010/029153 | 3/2010 |
| WO | WO 2010/029153 A1 | 3/2010 |
| WO | WO 2010/066660 | 6/2010 |

OTHER PUBLICATIONS

RD 436093, RD, Aug. 10, 2000, Akzo Nobel.

Ullmann's Encyclopedia of Industrial Chemistry, 2005, "pH Measurement and Control", Wiley-VCH GmbH & Co. KGaA, Weinheim, 10.1002/14356007.e19_e01; pp. 1-31 (32 pgs).

Medium and Long-Term Opportunities and Risks of the Biotechnologial Production of Bulk Chemicals from Renewable Resources—The Potential of White Biotechnology—The BREW Project—Final Report—Prepared under the European Commission's GRXTH Programme (DG Research) Utrecht, Sep. 2006 (pp. 29-31).

Ullmann Encyl. Industr. Chem., 5$^{th}$ Ed., vol. A6, (1988), pp. 401-477.

Polymer Science Dictionary, M,S.M., Elsevier Applied Chemistry, London and New York 1989, p. 86.

Perry's chemical Engineers' Handbook, Sixth Edition, Section 21, pp. 21-55,1996.

E. Millchert et al., "Installation for the Recovery of Dichloropropanois and Eplchlorohydrin from the Waste Water in Eplchlorohydrin Production", Pol. J. Appl. Chem., vol. 41, p. 113-118 (1997).

Klelboehmer W., et al, Solvay Werk Rheinberg: Integrierte Prozesse Separlerte Abwasserbehandiungen—Gewaesserschutz, Wasser, Abwasser 200 (Wissenschaftilich-technische Mitteilungen des Instituts Zur Foerderung der Wasserguerte- und Wassermengenwirtschaft e; V;-2005 p. 81/-8/5., vol. 5.

Klaus Weissermel, et al., "Industrial Organic Chemistry," (3$^{rd}$ Completely Revised Edition); VCH 1997. p. 93-98.

Klaus Weissermel, et al,, "Industrial Organic Chemistry," (3$^{rd}$ Completely Revised Edition); VCH 1997. p. 276-277.

Klaus Weissermel, et al., "Industrial Organic Chemistry," (3$^{rd}$ Completely Revised Edition); VCH 1997. p. 347-355.

Ying Ling Liu, "Epoxy Resins from Novel Monomers with a Bis-(9,10-dihydro-9-oxa-10-oxide-10-phosphaphenanthrene-10-yl-) Substituent," Journal of Polymer Science: Part A: Polymer Chemistry, vol. 40, 359-368 (2002).

Ying Ling Liu, "Phosphorous-Containing Epoxy Resins from a Novel Synthesis Route," Journal of Applied Polymer Science, vol. 83, 1697-1701 (2002).

M. Schellentrager, "Untersuchungen zur oxidation Entfarbung aus gewahlter Reaktivfarbstoffe: Analyse der Abbauprodukte misteels hochauflosender LC-MS", Dissertation, XP 0002548413 (Jan. 1, 2006) w/English Abstract.

U.S. Appl. No. 60/734,659, filed Nov. 8, 2005.
U.S. Appl. No. 60/734,627, filed Nov. 8, 2005.
U.S. Appl. No. 60/734,657, filed Nov. 8, 2005.

U.S. Appl. No. 60/734,658, filed Nov. 8, 2005.
U.S. Appl. No. 60/734,635, filed Nov. 8, 2005.
U.S. Appl. No. 60/734,634, filed Nov. 8, 2005.
U.S. Appl. No. 60/734,637, filed Nov. 8, 2005.
U.S. Appl. No. 11/915,046, filed Nov. 20, 2007, Krafft, et al.
U.S. Appl. No. 60/734,636, Nov. 8, 2005.
U.S. Appl. No. 11/915,088, filed Nov. 20, 2007, Krafft, et al.
U.S. Appl. No. 60/560,676, filed Apr. 8, 2004, Gilbeau, et al.
U.S. Appl. No. 61/013,680, filed Dec. 14, 2007, Krafft, et al.
U.S. Appl. No. 61/013,704, filed Dec. 14, 2007, Gilbeau, et al.
U.S. Appl. No. 61/013,676, filed Dec. 14, 2007, Borremans.
U.S. Appl. No. 61/013,707, filed Dec. 14, 2007, Krafft, et al.
U.S. Appl. No. 61/013,672, filed Dec. 14, 2007, Krafft, et al.
U.S. Appl. No. 61/013,713, filed Dec. 14, 2007, Gilbeau.
U.S. Appl. No. 61/013,710, filed Dec. 14, 2007, Krafft, et al.
U.S. Appl. No. 61/007,661, filed Dec. 14, 2007, Boulos, et al.
U.S. Appl. No. 12/529,777, filed Sep. 3, 3009, Krafft, et al.
U.S. Appl. No. 12/527,538, filed Aug. 17, 2009, Gilbeau, et.
U.S. Appl. No. 12/529,778, filed Sep. 3, 2009, Krafft, et al.
U.S. Appl. No. 12/663,749, filed Dec. 9, 2009, Krafft, et al.
U.S. Appl. No. 12/663,753, filed Dec. 9, 2009, Krafft, et al.
U.S. Appl. No. 12/663,887, filed Dec. 10, 2009, Krafft, et al.
U.S. Appl. No. 12/663,744, filed Dec. 9, 2009, Boulos, et al.
U.S. Appl. No. 12/681,083, filed Mar. 31, 2010, Bobet, et al.
Ma Zengxin et al, "recovery of Polyglycerol from residues of Synthetic Glycerol" Riyong Huaxue Gongye, 1997, 4. 21023 (English Abstract only).
Sang Hee Lee et al "Direct preparation of Dichloropropanol (DCP) from Glycerol Using Heteropolyacid (HPA) Catalysts: A Catalyst Screen Study," Catalysis Communications (9), 2008, p. 1920-1923.
Production and Prospect of the World Natural Glycerol by Zhu Shiyong, Cereals and Oils, vol. 1, 1997, pp. 33-38 (No English Translation).
Vinnolit: Vinnolit receives EU grant for water recycling project: Press Release, 2008: http://www.vinnolit.de/vinnolit.nsf/id/EN__Vinnolit_receives_EU_grant_for_water_recycling_project_.
N.W. Ziels, Journal of American Oil Chemists' Society, Nov. 1956. vol. 33, pp. 556-565.
Perry's Chemical Engineers Handbook, Sixth Edition, McGraw Hill Inc., (1984) Section 18.
Vol. B3: Unit Operations II of Ullmann's Encyclopedia of Industrial Chemistry, Fifth Completely Revised Edition, Published by VCH, 1988.
W. Giger et al., "14C/12C-Ratios in Organic Matter and Hydrocarbons Extracted from Dated Lake Sediments," Nuclear Instruments and Methods in Physics Research B5 (1984), 394-397, XP-002631954.
Jurgen O. Metzger, "Fats and Oils as Renewable Feedstock for Chemistry," Eur. J. Lipid Sci. Technol. (2009), 111, 865-876. XP-002631953.
Bruce M. Bell, "Glycerin as a Renewable Feedstock for Epichlorohydrin Production. The GTE Process," Clean-Soil, Air, Water, vol. 36, No. 6. (2008) pp. 657-661. XP-002631952.
Herman A. Bruson, et al., "Thermal Decomposition of Glyceryl Carbonates," Journal of the American Chemical Society, vol. 74, Apr. 1952 pp. 2100-2101.
Perry's Chemical Engineers Handbook 7th Ed., 11th Section, 1997, pp. 11.1-11.118 (submitted into two parts).
Perry's Chemical Engineers Handbook 7th Ed., 13th Section, 1997, pp. 13.1-13.108.
Perry's Chemical Engineers Handbook 7th Ed., 15th Section, 1997, pp. 15.1-15.47.
Ullmann'S Encyclopedia of Industrial Chemistry 5th Ed., vol A23, 1993, pp. 635-636.
Ullmann'S Encyclopedia of Industrial Chemistry 5th Ed., vol A13, 1989, p. 289.
Ullmann'S Encyclopedia of Industrial Chemistry 5th Ed., vol A11, 1988, pp. 354-360.
Attached certified copy of Application No. FR 06.05325 filed Jun. 14, 2006 by Solvay S.A.—priority document to EP2007/55742 published as WO 2007/144335 (attached herein) 17 pgs.
Attached certified copy of Application No. FR 07.53863 filed Mar. 15, 2007 by Solvay S.A. and published as FR2913683, 19 pgs (attached herein)—priority document to EP2007/55742 published as WO2007/144335 29 pgs (attached herein).
Gibson, "The preparation, properties, and uses of glycerol derivatives, Part III. The Chlorohydrins", 1931, Chemistry and Industry, Chemical Society, pp. 949-975.
Carre et al, 1931, "La transformation des alcools polyatomiques en mono-et en polychlorohydrines au moyen du chlorure de thionyle", Bulletin De La Societe Chimique De France, Societe Francaise De Chimie. Paris—ISSN 0037-8968, vol. 49, No. 49, pp. 1150-1154.
Fauconner, 1888, "Preparation de l'epichlorhydrine", Bull. Soc. Chim. FR, No. 50, pp. 212-214 (with enclosed translation in English).
Ullmann's Encyclopedia of Industrial Chemistry, "Industrially important epoxides", 1987, Fifth Completely Revised Edition, vol. A9, pp. 539-540.
Bonner et al, "The composition of constant boiling hydrochloric acid at pressures of 50 to 1220 millimeters", 1930, Journal of American Chemical Society, vol. 52, pp. 633-635.
Muskof et al, "Epoxy Resins" in Ullmann's Encyclopedia of Industrial Chemistry, 1987, 5th Ed., vol. A9, pp. 547-563.
Novelli, A., "The preparation of mono-and dichlorohydrins of glycerol", 1930, Anales Farmacia Bioquimica, vol. 1, pp. 8-19 (with English abstract).
Derwent Publications, AN 109:6092 CA, JP 62-242638, Oct. 23, 1987, 1 pg.
Derwent Publications, AN 1987-338139 [48], JP 62-242638, Oct. 23, 1987, 1 pg.
I. Miyakawa et al, Nagoya Sangyo Kagaku Kenkyusho Kenkyu Hokoku, 10, 49-52 (1957). (Abstract in English only). 1 pg.
Han Xiu-Ying et al, Shanxi Daxue Xuebao Bianjibu, 2002, 25(4), 379-80. (Abstract in English only), 1 pg.
Semendyaeva et al, 1981. Khimicheskaya Promyshlennost, Seriya: Khomaya Promyshlennost, 5. 21-2 (CA Summary). XP 002465275, 1 pg.
Rudnenko, EV, et al., 1988, Lakokrasochnye Materially i 1kh Primenenie, 4 69-71 (CA Summary) XP 002465276, 1 pg.
Kirk-Othmer Encyclopedia of Chemical Technology, 1978, 3rd Ed., vol. 4, Blood, Coagulants and Anticoagulants to Cardiovascular Agents. p. 847-848.
Jeffrey Lutje Spelberg, et al, A Tandem Enzyme Reaction to Produce Optically Active Halohydrins, Epoxides and Diols, Tetrahedron: Asymmetry, Elsevler Science Publishers, vol. 10, No. 15, 1999, pp. 2863-2870.
Oleoline.com. Glycerine Market report, Sep. 10, 2003, No. 62, 31 pgs.
Notification Under Act. No. 100/2001, Coll. as Amended by Act No. 93/2004, Coll. to the extent of Annex No. 4 (SPOLEK) Nov. 30, 2004, 80 pgs.
Documentation Under Act. No. 100/2001 Coll. as Amended by Act. No. 93/2004 Coll in the scope of appendix No. 4 (SPOLEK) Jan. 11, 2005, 86 pgs.
K. Weissermel & H.J. Arpe, Industrial Organic Chemistry, Third, Completely Revised Edition, VCH, 1997, pp. 149 & 275.
Industrial Bioproducts: "Today and Tomorrow." Energetics, Inc. for the U.S. Department of Energy, Office of Energy Efficiency and Renewable Energy, Office of the Biomass Program, Jul. 2003, pp. 49, 52 to 56.
Kirk Othmer Encyclopedia of Chemical Technology, Fourth Edition, 1992, vol. 2, p. 156, John Wiley & Sons, Inc.
Ullmann's Encyclopedia of Industrial Chemistry, Fifth, Completely Revised Edition, 1988, vol. A13, pp. 292-293.
The Merck Index, Eleventh Edition, 1989, pp. 759-760.
Ullmann's Encyclopedia of Industrial Chemistry, Fifth completely Revised Edition, vol. Al, 1985, pp. 427-429.
Ullmann's Encyclopedia of Industrial Chemistry, Fifth Completely Revised Edition, vol. A6, 1986, pp. 240-252.
Hancock, E.G., Propylene and its Industrial Derivatives, 1973, pp. 298-332.
K. Weissermel & H.J. Arpe, Industrial Organic Chemistry, Third, Completely Revised Edition, VCH 1997, pp. 149-163.
K. Weissermel & H.J. Arpe, in Industrial Organic Chemistry, Third, Completely Revised Edition, VCH 1997, pp. 275-276.
Robert T. Morrison & Robert N. Boyd, Organic Chemistry, 5th Ed., vol. II, pp. 666 to 667 and 712 to 714 (Japanese Translation), published on Jul. 10, 1970, Tokyo Kagaku Dozin Co., Ltd. (and similar passages but retrieved from the English Fifth Edition of the Book, 1987).
Perry's Chemical Engineers' Handbook, Sixth Edition, Robert H. Perry, Don Green, 1984, Section 21-64 to 21-68.
Iwanami et al, Dictionary of Physics and Chemistry, Third Edition, Ryo Midorikawa /Iwanami Shoten, Publishers, May 29, 1971, pp. 270-271, 595 and 726.
Expert Opinion on the Environment Impact Assessment Documentation Pursuant to Annex No. 5 of Act No. 100/2001 Coll., as amended by later regulations of the project/intent combined process for the manufacture of epichlorohydrin (SPOLEX) Apr. 2005.
Kirk Othmer Encyclopedia of Chemical Technology, Third Edition, vol. 12, 1980, pp. 1002-1005.
Chemical Engineering Handbook, the 6th Edition, Edited by the Society of Chemical Engineers, published by Maruzen Co, Ltd., 1999, pp. 1296-1306 Pub. Feb. 25, 1999 w/English translation of p. 1296, Table 28.4, p. 1298, left column, lines 4-13 and p. 1305, Table 28.10.
Product Brochure of De Dietrich Company, Apr. 1996, pp. 3, 8 and 9 w/English translation of p. 8, left column, lines 1-4, p. 9.
The Journal of the American Chemical Society, vol. XLV, Jul.-Dec. 1923, pp. 2771-2772.
Berichte Der Deutschen Chemischen Gesellschaft, 1891, vol. 24, pp. 508-510.
Catalogue of Nittetu Chemical Engineering Ltd. (Published in Mar. 1994).
12093 Chemicals, The Chemical Daily Co., Ltd. (Published on Jan. 22, 1993) with attached English translation of relevant excerpts, 24 pgs.
Chemicals Guide, Chemical Daily Co., Ltd. (Published on Jun. 15, 1990) with attached English translation of relevant excerpts.
[Unknown Author], Kirk Othmer Encyclopedia of Chemical Technology—vol. 2, p. 156, John Wiley and Sons, 1992.

U.S. Appl. No. 12/864,211, filed Jul. 27, 2010, Patrick Gilbeau, et al.
J.B. Conant, et al, "Glycerol a,y-dichlorohydrin", Organic Syntheses Coll., 1941, vol. 1, p. 292-294 (5 pp.).
Gilman H., Organic Synthesis, Section 1, pp. 234-235 (no date)—attached English translation only.
Industrial Chemical Encyclopedia 5, p. 457 (no date)—attached English translation only.
"Epoxy resins", p. 36-46, by Shangai Resin Plant, Shangai People's Press, 1971—attached English translation only.
Martinetti, R. et al. "Environnement Le Recyclage du l'eau" Industrie Textile, Ste Sippe Sarl, Metz, FR, No. 1300 (Jul. 1, 1998), ISSN: 0019-9176 (no English abstract available)—8 pp.
"Rainwater Harvesting and Utilization" (United Nations Environment Program) Mar. 2002; XP003003726; Internet Citation extracted online on Jan. 1, 2001: URL:http://www.unep.or.jp/letc/Publication—4 pp.
Myszkowski, J. et al. "Removal of chlorinated organic impurities from hydrogen chloride"; English Chemical Abstract summary only of Polish Patent No. 136598 B2 (Mar. 31, 1986); XP002352444; 1 pp.
Myszkowski, J. et al. "Removal of organic compounds from gaseous hydrogen chloride by an absorption method" Chemia Stosowana (1986) vol. 30(4) p. 545-51; English Chemical Abstract Summary only; XP002352445; 1 pp.
Milchert, E. et al. "Recovering hydrogen chloride and organic chloro compounds from the reaction mixture in the chlorination of ethylene"; English Chemical Abstract Summary only of Polish Patent No. 162910 B1 (Jan. 31, 1994); XP002352443; 1 pp.
Laine, D.F. et al. "The destruction of organic pollutants under mild reaction conditions; A review" Michochemical Journal, vol. 85, No. 2, 2007 pp. 183-193; available online Aug. 17, 2006; 12 pp.
U.S. Appl. No. 13/131,516, Patrick Gilbeau.
U.S. Appl. No. 13/060,421, filed Feb. 23, 2011, Dominique Balthasart et al.
U.S. Appl. No. 13/063,230, filed Mar. 10, 2011, Philippe Krafft et al.

(A) (B) (C) (D) (E) (F) (G)

(H) (I) (J) (K) (L) (M) (N)

PROCESS FOR MANUFACTURING A CHLOROHYDRIN

CROSS-REFERENCE TO RELATED APPLICATIONS

The present patent application is a U.S. national stage application under 35 U.S.C. §371 of International Application No. PCT/EP2008/056688 filed May 30, 2008, which claims the benefit of the patent application No. EP 07109461.9 filed on Jun. 1, 2007 and of the U.S. provisional patent application No. 61/013,676 filed on Dec. 14, 2007, the content of each of these applications being incorporated herein by reference for all purposes.

The present invention relates to a process for preparing a chlorohydrin. It relates more specifically to a process for preparing a chlorohydrin in a stirred reactor.

Chlorohydrins are reaction intermediates in the preparation of epoxides and derived products. Dichloropropanol, for example, is a reaction intermediate in the preparation of epichlorohydrin and of epoxy resins (Kirk-Othmer Encyclopedia of Chemical Technology, Fourth Edition, 1992, Vol. 2, page 156, John Wiley & Sons, Inc.).

According to known processes it is possible to obtain dichloropropanol in particular by hypochlorinating allyl chloride, by chlorinating allyl alcohol and by hydrochlorinating glycerol. This latter process has the advantage that the dichloropropanol can be obtained starting from fossil raw materials or from renewable raw materials, and it is known that natural petrochemical resources, from which the fossil materials are obtained, such as petroleum, natural gas or coal, for example, are limited in their terrestrial availability.

Patent application WO 2005/021476 describes a process for preparing dichloropropanol by reacting glycerol with gaseous hydrogen chloride in a liquid-gas type reactor. The dispersing devices disclosed for dispersing gaseous hydrogen chloride are nozzles, perforated plates or pipes, microporous plates and ejectors. To be efficient, i.e. to produce fine gas bubbles, such systems must present very small apertures which can easily be clogged either by insoluble matter in the liquid reaction medium or by corrosion products of the dispersion device by the corrosive gas.

The goal of the invention is to provide a process for manufacturing a chlorhydrin which does not suffer of such problems.

The invention is therefore related to a process for manufacturing a chlorohydrin by reacting a polyhydroxylated-aliphatic hydrocarbon, an ester of a polyhydroxylated-aliphatic hydrocarbon, or a mixture thereof with a chlorinating agent in a reactor containing a liquid reaction medium wherein the chlorinating agent is used at least partially in the gaseous form, and wherein said reactor is stirred by means of a stirring system comprising at least one radial-flow impeller and at least one axial-flow impeller.

By impeller, one intends to designate one that impels, as a rotating device used to force a fluid in a desired direction under pressure. A flat disk is not considered as being an impeller.

The stirring system contains often one radial-flow impeller and two axial-flow impellers and frequently two radial-flow impellers and one axial-flow impeller.

It has surprisingly been found that with such a stirring system:
a) a high dispersion of the gaseous chlorinating agent in the liquid reaction mixture can be obtained with no aperture size limitation to the gas injection system, thereby eliminating the risk of clogging problem of the injection device, and
b) a good mixing can be obtained in the liquid reaction medium.

Without being bound by any theory, it is believed that the radial-flow impeller allows a very efficient dispersion of small gas bubbles in the liquid even at high gas flow rates, while the axial-flow impeller ensures the homogeneous distribution of the small gas bubbles throughout the liquid reaction medium and a good homogenization of the liquid reaction mixture itself.

An additional advantage is that simpler geometry of the gas injection system are suitable, which are easier to cover or to manufacture in materials resistant to the chlorinating agent.

A further additional advantage of such a stirring system is that it is able to handle high gas rates without flooding. Flooding is the condition where the mixing system is not in control of the flow pattern in the liquid, rather the gas is in control.

Another further advantage of such a stirring system is that it can provide a high dispersion of the gaseous chlorinating agent in the liquid reaction mixture without a shroud or draft tube, which confines the flow pattern. The use of baffles along the walls of the reactor does not constitute shrouding of the stirring system.

For a detailed description of the present invention, reference will now be made to the accompanying drawings in which.

Figure 1:
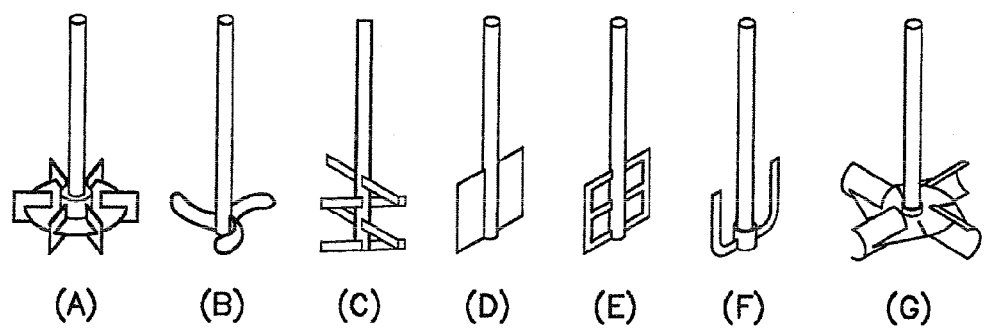
FIG. 1 illustrates various examples of radial-flow impellers (A)-(G) and various examples of axial-flow and mixed flow impellers (H)-(N) which can be used in the stirring system in accordance with the process of the present invention.
Figure 1:
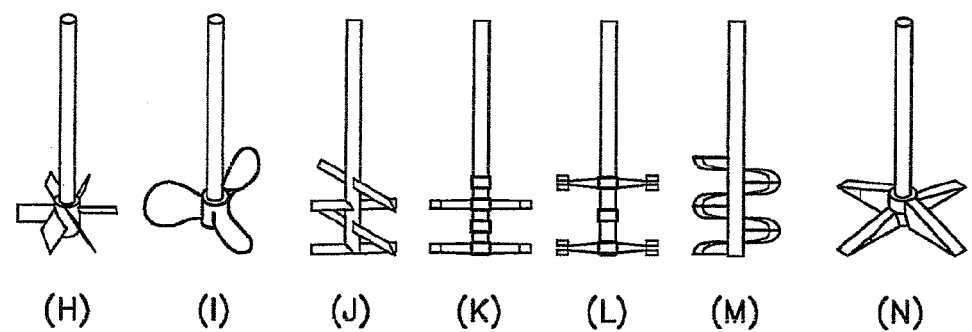

The term "polyhydroxylated aliphatic hydrocarbon" refers to a hydrocarbon which contains at least two hydroxyl groups attached to two different saturated carbon atoms. The polyhydroxylated aliphatic hydrocarbon may contain, but is not limited to, from 2 to 60 carbon atoms.

Each of the carbons of a polyhydroxylated aliphatic hydrocarbon bearing the hydroxyl functional group (OH) cannot possess more than one OH group and must have sp3 hybridization. The carbon atom carrying the OH group may be primary, secondary or tertiary. The polyhydroxylated aliphatic hydrocarbon used in the present invention must contain at least two sp3-hybridized carbon atoms carrying an OH group. The polyhydroxylated aliphatic hydrocarbon includes any hydrocarbon containing a vicinal diol (1,2-diol) or a vicinal triol (1,2,3-triol), including the higher, vicinal or contiguous orders of these repeating units. The definition of the polyhydroxylated aliphatic hydrocarbon also includes, for example, one or more 1,3-, 1,4-, 1,5- and 1,6-diol functional groups.

The polyhydroxylated aliphatic hydrocarbon may also be a polymer such as polyvinyl alcohol. Geminal diols, for example, are excluded from this class of polyhydroxylated aliphatic hydrocarbons.

The polyhydroxylated aliphatic hydrocarbons may contain aromatic moieties or heteroatoms, including, for example, heteroatoms of halogen, sulphur, phosphorus, nitrogen, oxygen, silicon and boron type, and mixtures thereof.

Polyhydroxylated aliphatic hydrocarbons which can be used in the present invention comprise, for example, 1,2-ethanediol (ethylene glycol), 1,2-propanediol (propylene glycol), 1,3-propanediol, 1-chloro-2,3-propanediol (chloropropanediol), 2-chloro-1,3-propanediol (chloropropanediol), 1,4-butanediol, 1,5-pentanediol, cyclohexanediols, 1,2-butanediol, 1,2-cyclohexanedimethanol, 1,2,3-propanetriol (also known as "glycerol" or "glycerin"), and mixtures thereof. With preference the polyhydroxylated aliphatic hydrocarbon used in the present invention includes, for example, 1,2-ethanediol, 1,2-propanediol, 1,3-propanediol, chloropropanediol and 1,2,3-propanetriol, and mixtures of at least two thereof. More preferably the polyhydroxylated aliphatic hydrocarbon used in the present invention includes, for example, 1,2-ethanediol, 1,2-propanediol, chloropropanediol and 1,2,3-propanetriol, and mixtures of at least two thereof. 1,2,3-Propanetriol or glycerol is the most preferred.

The esters of polyhydroxylated aliphatic hydrocarbon may be present in the polyhydroxylated aliphatic hydrocarbon and/or may be produced in the process for preparing the chlorohydrin and/or may be prepared prior to the process for preparing the chlorohydrin. Examples of esters of the polyhydroxylated aliphatic hydrocarbon comprise ethylene glycol monoacetate, propanediol monoacetates, glycerol monoacetates, glycerol monostearates, glycerol diacetates and mixtures thereof.

The term "chlorohydrin" is used here in order to describe a compound containing at least one hydroxyl group and at least one chlorine atom attached to different saturated carbon atoms. A chlorohydrin which contains at least two hydroxyl groups is also a polyhydroxylated aliphatic hydrocarbon. Accordingly the starting material and the product of the reaction may each be chlorohydrins. In that case the "product" chlorohydrin is more chlorinated than the starting chlorohydrin, in other words has more chlorine atoms and fewer hydroxyl groups than the starting chlorohydrin. Preferred chlorohydrins are chloroethanol, chloropropanol, chloropropanediol, dichloropropanol and mixtures of at least two thereof. Dichloropropanol is particularly preferred. Chlorohydrins which are more particularly preferred are 2-chloroethanol, 1-chloropropan-2-ol, 2-chloropropan-1-ol, 1-chloropropane-2,3-diol, 2-chloropropane-1,3-diol, 1,3-dichloropropan-2-ol, 2,3-dichloropropan-1-ol and mixtures of at least two thereof.

The polyhydroxylated aliphatic hydrocarbon, the ester of polyhydroxylated aliphatic hydrocarbon, or the mixture thereof in the process according to the invention may be obtained starting from fossil raw materials or starting from renewable raw materials, preferably starting from renewable raw materials.

By fossil raw materials are meant materials obtained from the processing of petrochemical natural resources, such as petroleum, natural gas and coal, for example. Among these materials preference is given to organic compounds containing 2 and 3 carbon atoms. When the polyhydroxylated aliphatic hydrocarbon is glycerol, allyl chloride, allyl alcohol and "synthetic" glycerol are particularly preferred. By "synthetic" glycerol is meant a glycerol generally obtained from petrochemical resources. When the polyhydroxylated aliphatic hydrocarbon is ethylene glycol, ethylene and "synthetic" ethylene glycol are particularly preferred. By "synthetic" ethylene glycol is meant an ethylene glycol generally obtained from petrochemical resources. When the polyhydroxylated aliphatic hydrocarbon is propylene glycol, propylene and "synthetic" propylene glycol are particularly preferred. By "synthetic" propylene glycol is meant a propylene glycol generally obtained from petrochemical resources.

By renewable raw materials are meant materials obtained from the processing of renewable natural resources. Among these materials preference is given to "natural" ethylene glycol, "natural" propylene glycol and "natural" glycerol. "Natural" ethylene glycol, propylene glycol and glycerol are obtained for example by conversion of sugars by thermochemical processes, it being possible for these sugars to be obtained starting from biomass, as described in "Industrial Bioproducts: Today and Tomorrow", Energetics, Incorporated for the U.S. Department of Energy, Office of Energy Efficiency and Renewable Energy, Office of the Biomass Program, July 2003, pages 49, 52 to 56. One of these processes is, for example, the catalytic hydrogenolysis of sorbitol obtained by thermochemical conversion of glucose. Another process is, for example, the catalytic hydrogenolysis of xylitol obtained by hydrogenation of xylose. The xylose may for example be obtained by hydrolysis of the hemicellulose present in maize fibres. By "glycerol obtained from renewable raw materials" is meant, in particular, glycerol obtained during the production of biodiesel or else glycerol obtained during conversions of animal or vegetable oils or fats in general, such as saponification, transesterification or hydrolysis reactions.

Among the oils which can be used in the process of the invention, mention may be made of all common oils, such as palm oil, palm kernel oil, copra oil, babassu oil, former or new (low erucic acid) colza oil, sunflower oil, maize oil, castor oil and cotton oil, peanut oil, soya bean oil, linseed oil and crambe oil, and all oils obtained, for example, from sunflower plants or colza plants obtained by genetic modification or hybridization.

It is also possible to employ used frying oils, various animal oils, such as fish oils, tallow, lard and even squaring greases.

Among the oils used mention may also be made of oils which have been partly modified by means, for example, of polymerization or oligomerization, such as, for example, the "stand oils" of linseed oil and of sunflower oil, and blown vegetable oils.

A particularly suitable glycerol may be obtained during the conversion of animal fats. Another particularly suitable glycerol may be obtained during the production of biodiesel. A third, very suitable glycerol may be obtained during the conversion of animal or vegetable oils or fats by transesterification in the presence of a heterogeneous catalyst, as described in documents FR 2752242, FR 2869612 and FR 2869613. More specifically, the heterogeneous catalyst is selected from mixed oxides of aluminium and zinc, mixed oxides of zinc and titanium, mixed oxides of zinc, titanium and aluminium, and mixed oxides of bismuth and aluminium, and the heterogeneous catalyst is employed in the form of a fixed bed. This latter process can be a process for producing biodiesel.

The chlorination agent generally comprises hydrogen chloride as described in WO 2005/054167, from page 4, line 30 to page 6, line 2, the content of which is incorporated herein by reference.

In the process according to the invention, the chlorinating agent is used at least partially in the gaseous form. It is often used completely in the gaseous form. Frequently the chlorinating agent used is gaseous hydrogen chloride or a mixture of gaseous hydrogen chloride and of a solution of hydrogen chloride. The solution of hydrogen chloride is often an aqueous solution.

In the process according to the invention, the reaction between the polyhydroxylated-aliphatic hydrocarbon, the ester of the polyhydroxylated-aliphatic hydrocarbon, or the mixture thereof with the chlorinating agent can be carried out as described in Patent Applications WO 2005/054167, WO 2006/100311, WO 2006/100312, WO 2006/100313, WO 2006/100314, WO 2006/100315, WO 2006/100316, WO 2006/100317, WO 2006/106153, WO 2007/054505, WO 2006/100318, WO 2006/100319, WO 2006/100320, WO 2006/106154, WO 2006/106155, WO 2007/054505 and FR 06/05325, all filed in the name of Solvay S A, and the contents of all of which are incorporated herein by reference.

Figure 2:
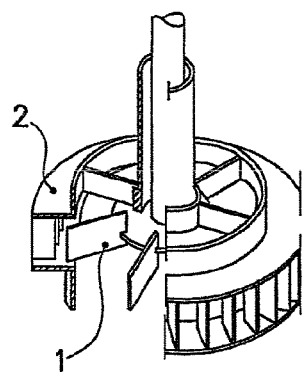
FIG. 2 illustrates a radial-flow impeller which is a rotor-stator stirrer which can be used in the stirring system in accordance with the process of the present invention.
Figure 4:
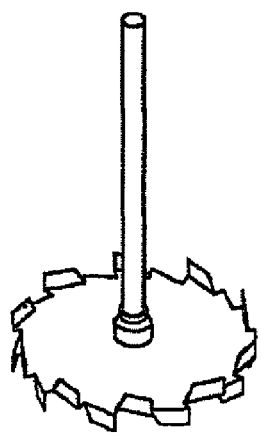
FIG. 4 illustrates a radial-flow impeller which is a toothed disk which can be used in the stirring system in accordance with the process of the present invention.

Radial-flow impellers have blades which are generally parallel to the axis of the drive shaft. Non limitative examples of radial-flow impellers are notably:

a) the turbine stirrer, such as the Rushton turbine comprising several flat blades on a disk (impeller (A) of FIG. 1), or such as the Smith turbine comprising several curved blades on a disk (impeller (G) on FIG. 1), which are advantageously high-speed stirrers that typically set the fluid in radial motion or, at higher viscosities, in tangential motion. This type of impellers are particularly effective with low-viscosity liquids and baffled vessels. For this type of impellers, the diameter ratio D/d (D=reactor vessel diameter; d=stirrer diameter) ranges advantageously from 2 to 5. During rotation, the turbine stirrers cause typically high levels of shear and is generally well suited to dispersion processes;

b) the impeller stirrer (impeller (B) of FIG. 1), which was notably developed in the past for use in enamel-coated vessels, and thus has rounded stirring arms. It is generally used in conjunction with small clearances from the bottom. For this type of impeller, the diameter ratio D/d ranges advantageously around 1.5 (that is to say between 1 and 2, preferably between 1.2 and 1.8, either with or without baffles. It can also operate with strongly fluctuating fill levels (e.g., during vessel discharging) because it is able to mix even small amounts of liquid;

c) the cross-beam impeller (impeller (C) of FIG. 1), the grid impeller (impeller (E) of FIG. 1), and the blade impeller (impeller (D) of FIG. 1), which advantageously belong to the group of low-speed stirrer types and are typically used with D/d from 1.5 to 2. They can operate with baffles or, especially for viscous media, without, and are especially well suited to homogenization;

d) the low-speed anchor stirrer (impeller (F) of FIG. 1), which is generally operated at very small clearances from the wall, that is to say at diameter ratio D/d from 1.005 to 1.5, preferably from 1.005 to 1.05 and is particularly appropriate for enhancing heat transfer in highly viscous media;

e) the rotor-stator stirrer or stirrer operating on the rotor-stator principle (FIG. 2), in which the rotor advantageously consists of a blade (1) or paddle stirrer (1) enclosed by a ring of baffles (stator) (2). As a result, high levels of shear are generally exerted on an extremely small volume;

f) the toothed disk (FIG. 4); using this stirrer, the liquid is advantageously accelerated radially in a thin ring away from the centre, and then quickly decelerated. High levels of shear can thus be achieved, even without a stator ring or baffles.

The radial-flow impeller is often chosen among the group consisting of a turbine stirrer, an impeller stirrer, a cross-beam impeller, a grid-impeller, a blade impeller, a low-speed anchor stirrer, a rotor-stator stirrer and a toothed disk. The radial-flow impeller is frequently chosen among the group consisting of a turbine stirrer, an impeller stirrer, a cross-beam impeller, a grid-impeller, a blade impeller.

The radial-flow impeller is more often a turbine stirrer, frequently a turbine stirrer of the Rushton type or a turbine stirrer of the Smith type, and more specifically a turbine stirrer of the Smith type. Such turbine comprises generally at least 2 curved blades on a disk and preferably at least 3 curved blades. The number of curved blades is generally of at most 10 and preferably of at most 8. A turbine with 6 curved blades on a disk is the most preferred turbine stirrer of the Smith type. A turbine with 4 curved blades on a disk is also very well suited. Without being bound by any theory, it is believed that another additional advantage of the curved blade radial-flow impeller selected is that it permits to insure a constant power draw when the gas flow rate varies inside a broad range. Under gassed conditions, this power draw is very close to the power draw achieved when there is no gas injection and therefore it avoids the over sizing of the whole cinematic chain (including the motor, the reducer, the shaft and the mechanical seal) and allows considerable investment savings.

The curved blades can be of any form, preferably hemi-cylindrical, hemi-cylindrical more or less flattened, and parabolic, and more preferably parabolic.

The distances between two successive blades can be equal or different. The distances are preferably equal.

By reference with the disk plane, the curved blades can be symmetrical or asymmetrical, preferably asymmetrical.

In general, the asymmetric radial-flow impeller will include a plurality of generally radially extending blades. Each of the blades will include upper and lower sheet-like portions which meet at a vertex, such that the cross-section of the blade will be generally parabolic or u-shaped. The width of the upper portion of each blade will be longer than the width of the lower portion making the blade asymmetric. Thus, at the leading edge of the blade there will be an upper portion overhang which can capture and disperse rising gas bubbles. The impeller can have any number of blades, but it is preferred that it has from 4 to 12 blades with 6 being most preferred. The upper sheet could extend 15 to 50 percent further than the width of the lower sheet, with about 25 percent being most preferred.

Figure 3:
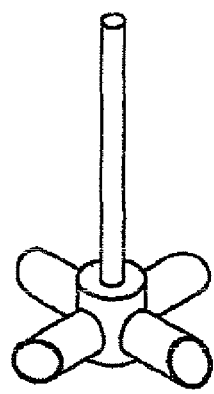
FIG. 3 illustrates an axial-flow impeller which is a hollow stirrer which can be used in the stirring system in accordance with the process of the present invention.

Axial-flow and mixed flow impellers include all impeller in which the blade(s) make(s) an angle of less than 90° with the plane of rotation. Non limitative examples of said impellers are notably:

a) the paddle stirrer with pitched blades (also known as pitched blade turbine) [impeller (H) of FIG. 1] and the propeller stirrer (also known as marine-type mixing propeller) [impeller (I) of FIG. 1], which typically belong to the group of high-speed mixers that advantageously generate an axial flow pattern. They are advantageously well suited to homogenization and suspension of solids and are typically used with D/d from 2 to 3.

b) multistage stirrers with pitched stirring surfaces such as the cross-beam stirrer with pitched beams [impeller (J) of FIG. 1] and the MIG stirrer [impeller (K) of FIG. 1] and INTER-MIG stirrer [impeller (L) of FIG. 1] of the Ekato company, Schopfheim, Germany, which are particularly suitable for enhancing the axial flow and/or for high liquid level to diameter ratios (H/D>1, wherein D=reactor vessel diameter; H=height of the liquid in the reactor vessel) are required. These stirrers are advantageously operated at low speeds. The diameter ratio for these stirrers D/d exceeds advantageously 1.5 when they are used in combination with baffles and is around 1.1 (that is to say between 1.005 and 1.5) when they are used without baffles.

c) the low-speed helical ribbon stirrer [impeller (M) of FIG. 1], which is generally used with small wall clearances (D/d>1.05) and typically operated in such a way that it drives the liquid downwards along the wall;

d) the hollow stirrer (FIG. 3), which typically has a hollow head and is connected through a hollow shaft to the gas-filled space above the liquid medium, And which is thus generally suitable for supplying a gas to a liquid; the suction generated behind the stirrer edges during rotation can be advantageously used to supply a gas in the reaction vessel;

e) the turbofoil impeller [impeller (N) of FIG. 1].

The axial-flow impeller is often chosen among the group consisting of a paddle-stirrer with pitched blades, a propeller stirrer (marine-type mixing propeller), a cross-beam stirrer with pitched beams, a MIG stirrer, an INTERMIG stirrer, a low-speed helical ribbon stirrer, a turbofoil impeller and a hollow stirrer.

The axial-flow impeller is frequently chosen among the group consisting of a paddle-stirrer with pitched blades, a propeller stirrer (marine-type mixing propeller), a MIG stirrer, an INTERMIG stirrer and a turbofoil impeller.

The axial-flow impeller is more often chosen among the group consisting of a paddle-stirrer with pitched blades, a propeller stirrer (marine-type mixing propeller) and a turbofoil impeller. The axial-flow impeller is more specifically a paddle-stirrer with pitched blades or a turbofoil impeller, and more particularly a turbofoil impeller.

The number of blades is generally higher than or equal to 2 and preferably higher than or equal to 3. That number is usually lower than or equal to 8 and preferably lower than or equal to 6. A number of 4 blades is particularly well suited.

The angle the blade(s) make(s) with the plane of rotation is preferably lower than or equal to 60°, more preferably lower than or equal to 55° and most preferably lower than or equal to 50°. That angle is generally higher than or equal to 30°, preferably higher than or equal to 35°, and more preferably higher than or equal to 40°. An angle of 45° is particularly well suited.

Hydrofoils impellers are a very important class of pitched blade turbines combining a bigger pumping capacity with a reduced power consumption. These performances are obtained by an optimized blade profile. Basically the angle of the trailing edge of the blade with the horizontal plane changes with the distance from the shaft like in an airplane propeller. In practice this angle change can be continuous or discontinuous. This allows a nearly uniform flow pattern at the discharge of the impeller and reduces the eddies at the trailing edge. Examples of hydrofoil impellers are Lightnin A 310, A 320 and A 340, Chemineer HE3, Philadelphia Mixers MHS & LS impellers, Pfaudler THF, Mixel TT, TTP and TTF.

The distances between two successive blades can be equal or different. The distances are preferably equal.

The sides of the blades can independently be flat, curved or facetted. A flat bottom oriented side and a two facetted top oriented side is more preferred.

Examples of such impellers are the pitched blade turbine (impeller (H), FIG. 1) and the turbofoil (impeller (N), FIG. 1). The turbofoil is the most preferred axial-flow impeller. It offers the additional advantage to be more easily coated, especially when glass-lined or enamelled coating is required.

In the stirring system of the process of the invention, the radial-flow impeller and the axial-flow impeller can be placed on a same shaft or on a different shaft. It is preferred that the radial-flow impeller and the axial-flow impeller are placed on a same shaft.

The stirring system of the invention can be placed in any position in the reactor, vertically, horizontally or obliquely, preferably vertically.

In the stirring system of the invention, the axial-flow impeller provides a flow of the liquid reaction medium which generally can be downwardly or upwardly, and is frequently downwardly.

In the stirring system of the process of the invention, the radial-flow impeller can be placed below or above the axial-flow impeller. It is preferred that the radial-flow impeller is placed below the axial-flow impeller. The diameter of the radial-flow impeller and of the axial-flow impeller depends on the reactor diameter.

The diameter of the radial-flow impeller is generally higher than or equal to one 33% of the reactor diameter, often higher than or equal to 40% of the reactor diameter and frequently higher than or equal to 50% of the reactor diameter. The diameter of the radial-flow impeller is generally lower than or equal to 70% of the reactor diameter, often lower than or equal to 65% of the reactor diameter and frequently lower than or equal to 55% of the reactor diameter.

The diameter of the axial-flow impeller is generally higher than or equal to 33% of the reactor diameter, often higher than or equal to 40% of the reactor diameter and frequently higher than or equal to 50% of the reactor diameter. The diameter of the axial-flow impeller is generally lower than or equal to 70% of the reactor diameter, often lower than or equal to 65% of the reactor diameter and frequently lower than or equal to 55% of the reactor diameter.

Those impeller diameter are measured between two opposite points on the outer periphery of the impeller.

The reactor diameter is the internal diameter of the reactor possibly diminished of the size of possibly present baffles.

The diameter of the radial-flow impeller and of the axial-flow impeller can be equal or different. When they are different, the diameter of the radial-flow impeller can be higher than or lower than the diameter of the axial-flow impeller. The diameter of the radial-flow impeller is often higher than the diameter of the axial-flow impeller. The diameter of the radial-flow impeller and of the axial-flow impeller are frequently equal.

The distance between the radial-flow impeller and the axial-flow impeller depends on the reactor height and on the impeller diameter.

When the radial-flow impeller and the axial-flow impeller have the same diameter, that distance is generally higher than or equal to one quarter of the impeller diameter, preferably higher than or equal to one third of the impeller diameter and more preferably higher than or equal to one half of that diameter. That distance is generally lower than or equal to two times the impeller diameter, and preferably lower than or equal to 1.5 times the impeller diameter. A distance equal to the impeller diameter is particularly well suited.

When the radial-flow impeller and the axial-flow impeller do not have the same diameter, that distance is generally higher than or equal to one quarter of the impeller highest diameter, preferably higher than or equal to one third of that impeller diameter and more preferably higher than or equal to one half of that diameter. That distance is generally lower than or equal to two times the impeller highest diameter, and preferably lower than or equal to 1.5 times the impeller diameter. A distance equal to the impeller diameter is particularly well suited.

In the process according to the invention, the stirring system may contain one radial-flow impeller and two axial-flow impellers or two radial-flow impellers and one axial flow impeller.

When the stirring system contains one radial-flow impeller and two axial-flow impellers, the axial-flow impellers can be different or identical. They are often identical. For that stirring system, the impellers are often placed on a same shaft and the radial-flow impeller is frequently placed below the two axial-flow impellers.

When the stirring system contains two radial-flow impellers and one axial-flow impeller, the radial-flow impellers can be different or identical. They are often identical. For that stirring system, the impellers are often placed on a same shaft and the radial-flow impellers are frequently placed below the axial-flow impeller.

In the process according to the invention, the chlorination agent can be injected anywhere in the reactor with respect to the radial- and/or axial flow impellers.

When the stirring system contains one radial-flow impeller and one axial flow impeller, the radial-flow impeller being located below the axial-flow impeller, the chlorination agent is injected generally below the level of the radial-flow impeller, often at the level of the radial-flow impeller and sometimes between the levels of the radial- and axial flow impellers.

When the stirring system contains one radial-flow impeller and two axial flow impellers, the radial-flow impeller being located below the axial-flow impellers, the chlorination agent is injected generally below the level of the lowest radial-flow impeller, often at the level of the radial-flow impeller and sometimes between the levels of the radial- and the lowest axial flow impeller.

When the stirring system contains two radial-flow impellers and one axial flow impeller, the radial-flow impellers being located below the axial-flow impeller, the chlorination agent is injected generally below the level of the lowest radial-flow impeller, often at the level of the lowest radial-flow impeller, sometimes between the levels of the radial-flow impellers, usually at the level of the highest radial-flow impeller, and commonly between the levels of the highest radial-flow impeller and the axial flow impeller.

In the process according to the invention, the injection of the chlorination agent in the reactor can be a single point injection or a multiple points injection.

A preferred single point injection level below the level of the lowest radial-flow impeller is more frequently used.

The injection of the chlorination agent can be carried out by any means, like through a perforated ring or a central tube. The injection is often carried out by a central tube.

Figure 5:
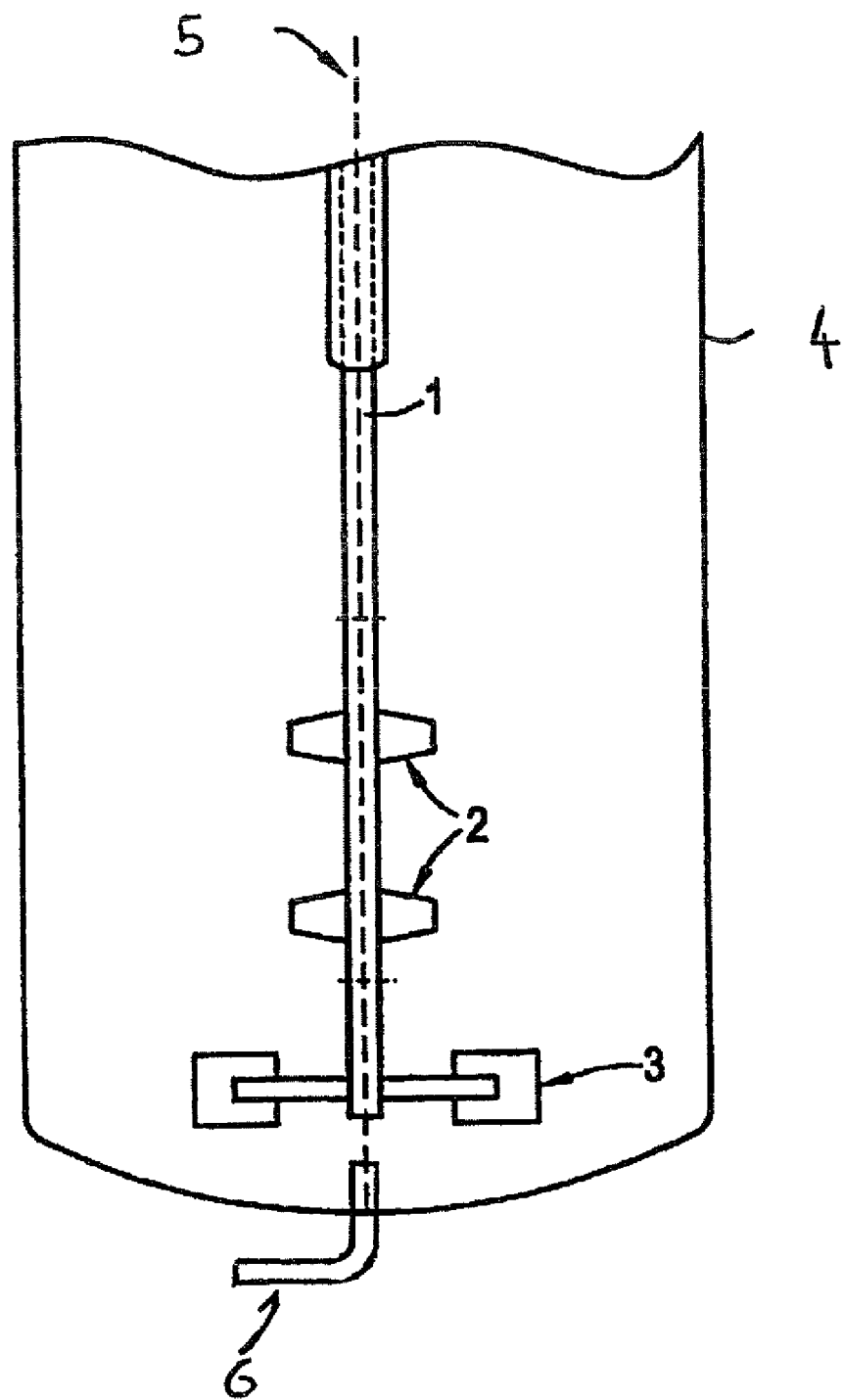
FIG. 5 illustrates a diagrammatic, sectional front elevation view of a reactor containing a stirring system in accordance with the process of the present invention.

A diagrammatic, sectional front elevation view of a reactor containing a stirring system in accordance with the process of the invention, is presented at FIG. 5, where (1) is a shaft, (2) are axial-flow impellers, (3) is a radial-flow impeller, (4) is the reactor, (5) is the shaft's axis and (6) is a pipe for injecting the chlorinating agent.

The speed of rotation of the stirring system will be set as a function of the stirring system type and reaction vessel diameter according to good practices well-known to the skilled in the art.

It will be generally preferred that the energy density obtained with the stirring system is of advantageously at least 0.5 kW/m$^3$ of liquid reaction medium, preferably at least 1 kW/m$^3$, more preferably at least 1.2 kW/m$^3$.

In general the energy density obtained with the stirring system is of advantageously at most 2 kW/m$^3$ of liquid reaction medium, preferably at most 1.5 kW/m3, more preferably at most 1.3 kW/m3.

The speed of rotation of the stirring device can vary in a broad domain; generally, the speed of rotation is of advantageously at least 30 rpm, preferably at least 50 rpm, more preferably of at least 70 rpm and is of advantageously at most 350 rpm, preferably of at most 300 rpm, more preferably of at most 250 rpm.

In particular, for a reactor having a diameter of from 1000 to 4000 mm, the speed of rotation of the impeller is advantageously selected between 50 and 200 rpm.

In the process according to the invention, the stirring system can be made of any material. That system is preferably made of or covered with materials which are resistant to the chlorinating agent, under the conditions of reaction.

The materials that are resistant, under the conditions of reaction, to the chlorinating agent, are selected from enamelled steel, polymers, coatings by means of resins, metals or alloys, ceramics and metalloceramics, refractory materials and graphite.

These materials are such as described in the patent applications WO2005/054167 and WO2006/100317 of SOLVAY S A, the contents of which are incorporated herein by reference.

The polymers can be selected from polyolefins, fluorinated polymers and polymers containing sulphur. The polyolefins are often selected from polyethylene and polypropylene. Polypropylene is preferred. The fluorinated polymers are frequently selected from polytetrafluoroethylene, poly(vinylidene fluoride) and poly(perfluorovinylether). Polytetrafluoroethylene, and poly(perfluorovinylether) are more frequently used. The polymers containing sulphur are often selected from polysulfones and polysulfides, aromatic or aliphatic. Aromatic polysulfones or polysulfides are more often used.

The coating by resins are often coatings by epoxy or phenolic resins, frequently coating by phenolic resins.

The metals are generally selected from tantalum, titanium, nickel, copper, gold, silver and molybdenum, often selected from tantalum, nickel, copper, gold, silver and molybdenum, frequently selected from tantalum, gold, silver and molybdenum, more frequently selected from tantalum and molybdenum. Tantalum is a particularly convenient metal.

The alloys are usually selected from alloys containing nickel and molybdenum. Hastelloy B is a convenient nickel-molybdenum alloy.

Graphite generally can be non-impregnated or impregnated graphite. Impregnated graphite is particularly convenient. Graphite can be impregnated with any material like for instance polytetrafluoroethylene or phenolic resins.

The preferred material for the stirring system is enamelled or glass-lined steel.

The invention is also related to a stirring system comprising at least one radial-flow impeller and one axial-flow impeller. The stirring system exhibits the characteristics described hereinabove.

The invention is finally related to the use of a stirring system comprising at least one radial-flow impeller and one axial-flow impeller for dispersing a gas in a liquid.

The examples below are intended to illustrate the invention, but without imposing any limitation thereon.

EXAMPLE 1

In Accordance with the Invention

A vessel with a diameter T of 3000 mm, a total height of 9200 mm (including top and bottom decimal heads) and a height of the cylindrical part of 8000 mm is equipped with a stirring system comprising one radial-flow impeller of the Rushton type comprising six flat blades and having a diameter $D_R$ of 1500 mm, and one axial-flow impeller of the turbofoil type comprising four blades and having a diameter of $D_A$ 1500 mm. Both impellers are placed on the same shaft. The radial flow impeller is placed below the axial flow impeller.

The stirring system is placed vertically in the reactor as presented in FIG. 5. The distance between the axial flow impeller and the top of the liquid is sufficient to avoid a vortex.

The vessel is filled with 33 m³ of a liquid having a density of 1000 kg/m³ and a viscosity of 2 cp. A gas with a density of 2.5 kg/m³ is injected at a flow rate Qg of 2000 kg/h (0.222 m³/s) in the liquid below the radial flow impeller.

We can calculate, for the stirring system, the following quantities:
1. the flooding speed (Nf) which is the minimal speed to avoid flooding
2. the complete dispersion speed (Ncd) which is the minimal speed to achieve complete dispersion of the gas
3. the actual speed (N) which is the nearest speed above the complete dispersion speed according to the American Gear Manufacturers Association
4. the power draw at actual speed under no gas conditions for the radial-flow impeller $(Pu)_R$
5. the minimal motor power $(Pmu)_R$ at actual speed under no gas conditions for the radial-flow impeller
6. the actual motor power at actual speed for the radial-flow impeller $(Pm)_R$
7. the power draw at actual speed under gas conditions for the radial-flow impeller $(Pg)_R$
8. the power draw at actual speed under no gas conditions for the axial-flow impeller $(Pu)_A$
9. the minimal motor power at actual speed under no gas conditions for the radial-flow and the axial-flow impellers $(Pmu)_{RA}$
10. the actual motor power at actual speed for the radial-flow and axial-flow impellers $(Pm)_{RA}$ using the following equations:
1. $Nf=(Qg*9.81*((T/D_R)^{3.5})/(30*(D_R^4)))^{0.3333}$ where Nf is the flooding speed (sec$^{-1}$) and Qg is the volumetric gas flow rate (m³/sec), for the Rushton radial-flow impeller
2. $Ncd=(Qg*((T*9.81/D_R)^{0.5})/(0.2*(D_R^{3.5})))^{0.5}$ where Ncd is the complete dispersion speed (sec$^{-1}$)
3. $(P_u)_R=Npo*\rho*(N^3)*(D_R^5)$ where Npo is the power number of the impeller (given by manufacturer and most of the time accessible in open literature: 5.5 for a Rushton turbine of 1500 mm of diameter), N is the actual impeller speed (sec$^{-1}$), $\rho$ is the liquid density (kg/m³) and $(P_u)_R$ is the absorbed power (W)
4. $(Pm)_R=1.2\ (Pu)_R$
5. $(Pg)_R=0.7\ (Pu)_R$ for a gassing number Fl and another adimensional number Fl3-3 such that Fl3-3<Fl<0.1 where
   a. $Fl=Qg/(N*(D_R^3))$
   b. $Fl3-3=0.0038*((T/D_R)^{0.5})*((Re^2)/Fr)^{0.07}$ where
      i. $Re=N*D_R^2*\rho/\mu$ is the Reynolds number with $\mu$ is the liquid viscosity (Pa*sec)
      ii. $Fr=(D_R*N^2)/9.81$ is the Froude number
6. $(P_u)_A=Npo*\rho*(N^3)*(D_A^5)$ where Npo is the power number of the impeller (given by manufacturer and most of the time accessible in open literature: 0.38 for a turbofoil impeller of 1500 mm of diameter), N is the actual impeller speed (seq$^{-1}$), $\rho$ is the liquid density (kg/m³) and $(P_u)_A$ is the absorbed power (W)
7. $(Pu)_{RA}=(Pu)_R+(Pu)_A$
8. $(Pm)_{RA}=1.2\ (Pu)_{RA}$ The results of the calculations are summarized in Table 1.

EXAMPLE 2

In Accordance with the Invention

The conditions are identical to those of example 1 except that the radial-flow impeller is of the Smith type and comprises six asymmetric parabolic curved blades and the equations used are:

1. $Nf=(Qg*9.81*((T/D_R)^{3.5})/(70*(D_R^4)))^{0.3333}$ where Nf is the flooding speed (sec$^{-1}$) and Qg is the volumetric gas flow rate (m³/sec), for the Smith radial-flow impeller
2. $Ncd=(Qg*((T*9.81/D_R)^{0.5})/(0.4*(D_R^{3.5})))^{0.5}$ where Ncd is the complete dispersion speed (sec$^{-1}$)

and Npo=2.3 for a Smith turbine.

The results of the calculations are summarized in Table 1.

TABLE 1

|  | Rushton/Turbofoil Exemple 1 | Smith/Turbofoil Exemple 2 | |
|---|---|---|---|
| Nf (rpm) | 32.7 | 24.7 | 24.7 |
| Ncd (rpm) | 65.4 | 46.3 | 46.3 |
| N (rpm) | 68 | 68 | 56 |
| $(Pu)_R$ (kW) | 60.8 | 25.4 | 14.2 |
| $(Pmu)_R$ (kW) | 73.0 | 30.5 | 17.0 |
| $(Pm)_R$ (kW) | 75.0 | 37.0 | 18.5 |
| $(Pg)_R$ (kW) | 42.6 | 22.9 | 12.8 |
| $(Pu)_A$ (kW) | 4.2 | 4.2 | 2.4 |
| $(Pmu)_{RA}$ (kW) | 78.0 | 35.5 | 19.9 |
| $(Pm)_{RA}$ (kW) | 90 | 37 | 22 |

EXAMPLE 3

In Accordance with the Invention

The conditions are identical to those of example 1 except that two radial flow impellers of the Rushton type having an equal diameter $D_R$ of 1500 mm and an axial flow impeller of the turbofoil type having a diameter $D_A$ of 1500 mm are used. The three impellers are placed on the same shaft. The radial flow impellers are placed below the axial flow impeller. The stirring system is placed vertically in the reactor. The distance between the axial flow impeller and the top of the liquid is sufficient to avoid a vortex.

The gas flowrate is split equally between the two radial flow impellers (1000 kg/hr for each) and the gas is injected in the liquid below each radial flow impeller.

The results of the calculations are summarized in Table 2.

TABLE 2

| Nf (rpm) | 26 |
|---|---|
| Ncd (rpm) | 46.3 |
| N (rpm) | 56 |
| $(Pu)_R$ (kW) | 68 |
| $(Pmu)_R$ (kW) | 82 |
| $(Pm)_R$ (kW) | 90.0 |
| $(Pg)_R$ (kW) | 61 |
| $(Pu)_A$ (kW) | 2.4 |
| $(Pmu)_{RA}$ (kW) | 84.5 |
| $(Pm)_{RA}$ (kW) | 90 |

EXAMPLE 4

In Accordance with the Invention

The conditions are identical to those of example 3 except that two radial flow impellers of the Smith type as in example 2 are used. The results of the calculations are summarized in Table 3.

TABLE 3

| Nf (rpm) | 20 |
|---|---|
| Ncd (rpm) | 32.7 |
| N (rpm) | 37 |

TABLE 3-continued

| | |
|---|---|
| $(Pu)_R$ (kW) | 8.2 |
| $(Pmu)_R$ (kW) | 9.8. |
| $(Pm)_R$ (kW) | 11.0 |
| $(Pg)_R$ (kW) | 7.4 |
| $(Pu)_A$ (kW) | 0.7 |
| $(Pmu)_{RA}$ (kW) | 10.7 |
| $(Pm)_{RA}$ (kW) | 11 |

EXAMPLE 5

Not in Accordance with the Invention

The conditions of example 1 have been used except that a single axial flow impeller, i.e. a pitch blade turbine comprising four flat blades with the blades making an angle of 45° with the plane of rotation is used. The diameter of the axial flow impeller $D_A$ is 1500 mm. No radial flow impeller is present. The stirring system is placed vertically in the reactor. The distance between the axial flow impeller and the top of the liquid is sufficient to avoid a vortex. The gas is injected below the axial-flow impeller.

For this type of axial flow impeller pumping downward, we have:

$$Nf=11.7*(QG)^{0.5}/(D_R)^{1.63}$$

$$Nf=Ncd$$

The results of the calculations are summarized in Table 4.

TABLE 4

| | |
|---|---|
| Nf (rpm) | 120 |
| Ncd (rpm) | 120 |
| N (rpm) | 125 |
| $(Pu)_A$ (kW) | 110 |
| $(Pmu)_{RA}$ (kW) | 132 |
| $(Pm)_{RA}$ (kW) | 132 |

The invention claimed is:

1. A process for manufacturing a chlorohydrin by reacting a polyhydroxylated-aliphatic hydrocarbon, an ester of a polyhydroxylated-aliphatic hydrocarbon, or a mixture thereof with a chlorinating agent in a reactor containing a liquid reaction medium wherein the chlorinating agent is used at least partially in the gaseous form, and wherein said reactor is stirred by means of a stirring system comprising at least one radial-flow impeller and at least one axial-flow impeller.

2. The process according to claim 1, wherein the radial-flow impeller is selected from the group consisting of a turbine stirrer, an impeller stirrer, a cross-beam impeller, a grid-impeller, a blade impeller, a low-speed anchor stirrer, a rotor-stator stirrer, and a toothed disk.

3. The process according to claim 1 wherein the axial-flow impeller is selected from the group consisting of a paddle-stirrer, a propeller stirrer, a multi-stage stirrer with pitched stirring surface, a MIG stirrer, an INTERMIG stirrer, a low-speed helical ribbon stirrer, a turbofoil impeller, and a hollow stirrer.

4. The process according to claim 2, wherein the radial-flow impeller is a turbine stirrer of the Smith type comprising from two to ten curved blades on a disk.

5. The process according to claim 3, wherein the axial-flow impeller is a paddle stirrer or a turbofoil impeller comprising from two to eight blades making an angle from 30 to 60° with the plane of rotation.

6. The process according to claim 4, wherein the curved blades of the turbine stirrer are of hemicylindrical or parabolic form and asymmetrical by reference with the disk plane.

7. The process according to claim 1, wherein the radial-flow impeller and the axial-flow impeller are placed on a same shaft.

8. The process according to claim 1, wherein the radial-flow impeller is located below the axial-flow impeller.

9. The process according to claim 1, wherein the axial-flow impeller provides a flow of the liquid reaction medium downwardly.

10. The process according to claim 1, wherein the stirring system is made of or covered with materials which are resistant to the chlorinating agent, under the conditions of reaction.

11. The process according to claim 10, wherein the materials that are resistant, under the conditions of reaction, to the chlorinating agent, are selected from the group consisting of enamelled (glass-lined) steel, polymers, coatings by means of resins, metals or alloys, ceramics and metalloceramics, refractory materials, and graphite.

12. The process according to claim 1, wherein two axial-flow impellers and one radial flow-impeller are located on a same shaft, the two axial-flow impellers being located above the radial-flow impeller.

13. The process according to claim 1, wherein one axial-flow impeller and two radial-flow impellers are located on a same shaft, the axial-flow impeller being located above the radial-flow impellers.

14. The process according to claim 1, wherein the chlorinating agent is injected in the reactor below the radial-flow impeller.

15. The process according to claim 1, wherein the chlorinating agent comprises hydrogen chloride.

* * * * *